United States Patent [19]
Muennemann et al.

[11] Patent Number: 5,143,068
[45] Date of Patent: Sep. 1, 1992

[54] FLEXIBLE AND CURVED RADIO FREQUENCY (RF) COIL FOR THE HUMAN SHOULDER FOR MAGNETIC RESONANCE IMAGING APPARATUS

[75] Inventors: Frank Muennemann, Menlo Park, Calif.; Rodney Bell, Kalamazoo, Mich.

[73] Assignee: Resonex, Inc., Sunnyvale, Calif.

[21] Appl. No.: 617,902

[22] Filed: Nov. 26, 1990

[51] Int. Cl.$^5$ .............................................. A61B 5/055
[52] U.S. Cl. .................................. 128/653.5; 324/318
[58] Field of Search ...................... 128/653 SC, 653.5; 324/318, 322

[56] References Cited
U.S. PATENT DOCUMENTS

| | | | |
|---|---|---|---|
| 4,734,647 | 3/1988 | Yoshimura | 324/318 |
| 4,791,372 | 12/1988 | Kirk et al. | 324/318 |
| 4,793,356 | 12/1988 | Misic et al. | 128/653 |
| 5,050,605 | 9/1991 | Eydelman et al. | 128/653 SC |

*Primary Examiner*—Ruth S. Smith
*Attorney, Agent, or Firm*—Flehr, Hohbach, Test, Albritton & Herbert

[57] ABSTRACT

A flexible, conformally fitted coil for imaging of the human shoulder and topologically similar specimens is in the form of a band of flexible conductive foil covered by a soft flexible insulating material. The geometry of the coil is such that it can pass under the arm and over the top of the shoulder, providing high sensitivity for magnetic resonance imaging (MRI) studies of the shoulder in MRI apparatus having either a vertical or horizontal axial magnetic field. The flexibility of the coil and the generality of its geometry makes it suitable for examination of patients in a wide variety of sizes. Radio Frequency (RF) Power is delivered to and/or received from the coil via a matching network. The matching network may include a transformer to reduce the necessary current delivered to the coil, or RF current may be injected directly into and extracted directly from the coil. In the case where a transformer is used, the secondary winding is incorporated into the coil in such a fashion as to make the flexible coil removable and replaceable without direct electrical contacts.

6 Claims, 2 Drawing Sheets

FLEXIBLE AND CURVED RADIO FREQUENCY (RF) COIL FOR THE HUMAN SHOULDER FOR MAGNETIC RESONANCE IMAGING APPARATUS

BACKGROUND OF THE INVENTION

The present invention is directed to magnetic resonance imaging (MRI) apparatus and more specifically flexible conformally fitted radio frequency (RF) coils.

Flexible coils as described in U.S. Pat. No. 4,791,372 and PCT International Application 8701199 are used to match the shape of the coil to various specimens or sized human patients. The nature of the flexible coil makes it possible to uniformly fill the coil with the specimen in an optimal manner.

For samples of a geometry which does not easily conform to the shape of a generalized cylinder (i.e. one having a non-circular cross-section), it is difficult to achieve optimal filling of the coil by the specimen.

OBJECT AND SUMMARY OF THE INVENTION

It is a general object of the present invention to provide improved imaging of the human shoulder and topologically similar specimens.

In accordance with the above object, there is provided a shoulder coil assembly having a predetermined magnetic axis for transmitting and/or receiving signals from a human shoulder produced in a magnetic resonance imaging apparatus comprising inductive pickup coil means for substantially surrounding said test specimen including a thin, flexible, unitary, continuous band of conductive material substantially entirely covered with a flexible protective material. The central portion of the band is shaped to conform to the side of the human thorax and pass around the base of the arm and includes a half turn in the central portion. The ends of the band are formed into connectors for connection to RF cables for injection and/or extraction of the signals. The protective cover has facing interiors provided with mutually adhering surfaces which, when fastened together, provide a conforming fit of the band to the top of the shoulder being imaged.

DESCRIPTION OF PREFERRED EMBODIMENTS

Figure 1:
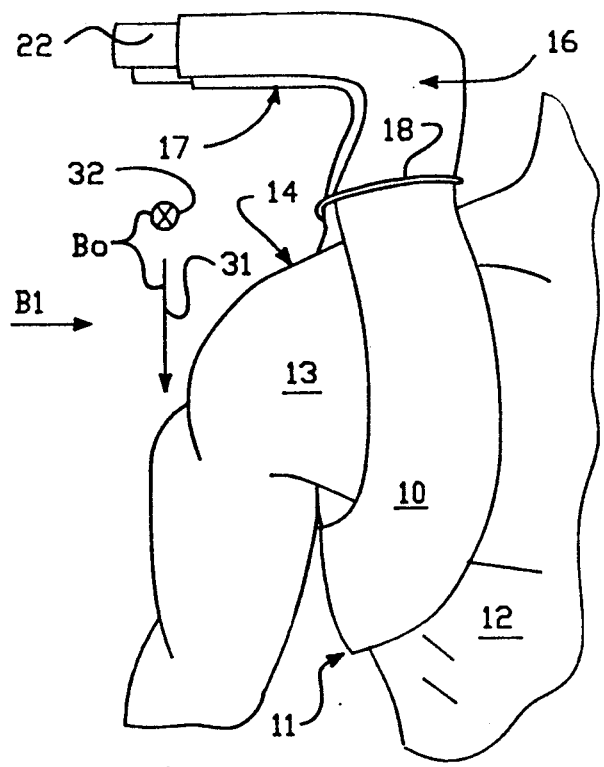
FIG. 1 is a plan perspective view of apparatus incorporating the present invention with a human specimen.

FIG. 1 illustrates the inductive pickup coil surrounding the test specimen which in this case is a human shoulder. The central portion 11 of the coil is shaped so that it conforms to the side of the human thorax 12, passes around the base of the arm at 13, and then over the top of the shoulder at 14 where the ends 16 and 17 of the band are adhered together to form a conforming fit at the shoulder top 14. Such adherence as will be described below is provided by a VELCRO fastening which has hooks and loops. Also a plastic clip 18 may be provided for locally assuring additional adherence. Thus far as described, the band 10 is of similar construction to that illustrated in the above mentioned U.S. Pat. No. 4,791,372.

Figure 2:
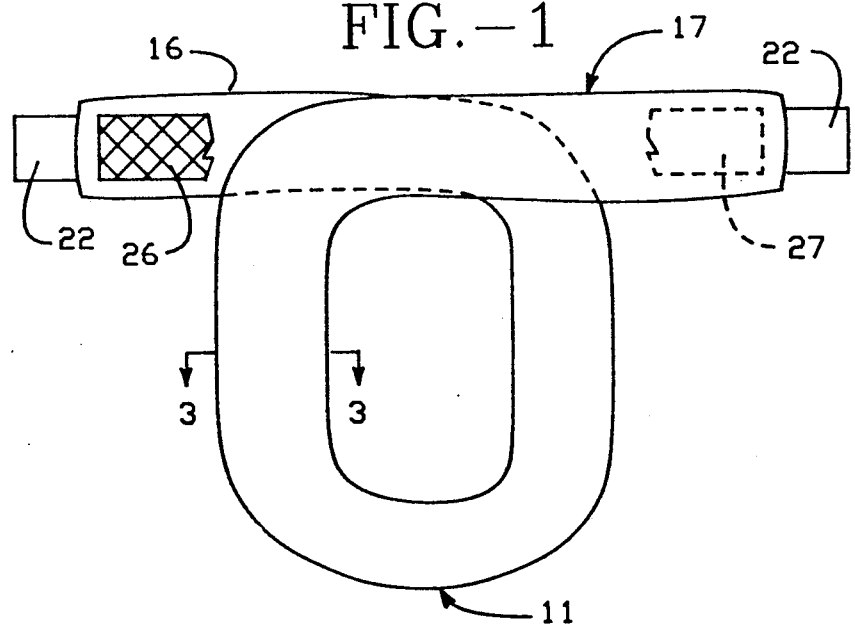
FIG. 2 is a top view of the coil or band portion of FIG. 1 laid flat.
Figure 3:
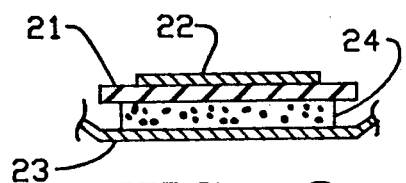
FIG. 3 is a partial cross-section taken substantially along the line 3—3 of FIG. 2.

Specifically, as illustrated in FIG. 3 in cross-sectional form, on the plastic base 21 there is a thin copper band of conductive material 22 entirely covered with flexible protective clothlike material 23. Specifically referring to FIG. 2, at the end 16, there is a VELCRO fastening segment 26 (which may be, for example, hooks) and as shown in - 27 there will be a matching loop of VELCRO fastening. This provides the units illustrated in FIG. 1. The difference between the above mentioned patent and the present invention as illustrated in FIG. 3 is that the padding or sponge material 24 facing the band from the shoulder is formed as part of the cloth protective cover and attached to the protective cover 23. Such facing as provided by this padding assures a more uniform RF signal as also shown in the '372 patent.

Referring now again to FIG. 2 a more significant difference between the above '372 patent is that the central portion 11 is given a half turn or a twist. This is clearly shown in FIG. 2 by the flat layout. Were it not for the turn or twist, the coil band would not conform and assuming it were a uniform band such as illustrated in the above '372 patent, it would require some compensating folds; this, of course, distorts the magnetic field.

The thickness of foil 21 is chosen to be substantially less than an electromagnetic depth at frequencies used by the MRI gradients but substantially greater than the electromagnetic skin depth at the frequencies of the RF excitation. This is claimed and discussed in U.S. Pat. No. 4,916,399, also assigned to the present assignee.

Referring back briefly to FIG. 1, the coil 10 as wrapped around a human shoulder is suitable for MRI apparatus having either a vertical or horizontal axial magnetic field as shown by the Bo vectors 31 or 32. Both of these are suitable for the coil 10 which has an effective magnetic axis B1 as illustrated in FIG. 1.

In summary the flexibility of coil 10 and the generality of its geometry makes it suitable for examination of patients in the shoulder area in a wide variety of sizes.

Figure 4:
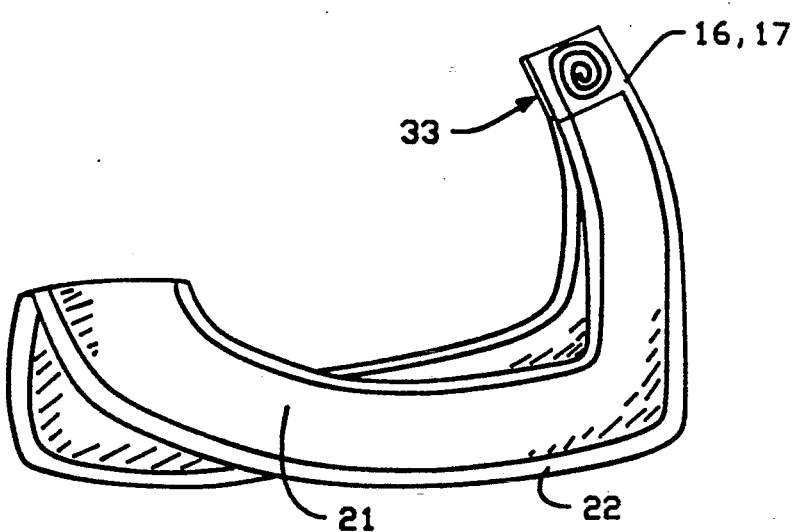
FIG. 4 is a perspective view illustrating the band of FIG. 2 without its protective covering and showing an alternative embodiment of an end connection.
Figure 5:
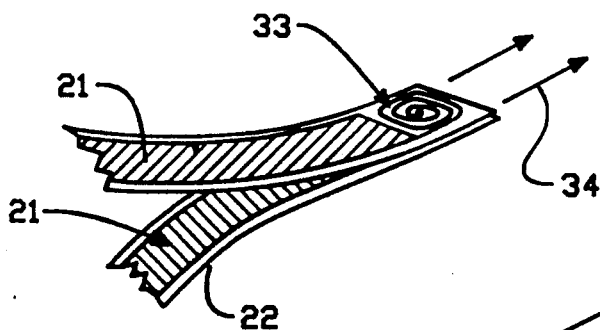
FIG. 5 is a perspective view showing an end portion of FIG. 4.
Figure 6:
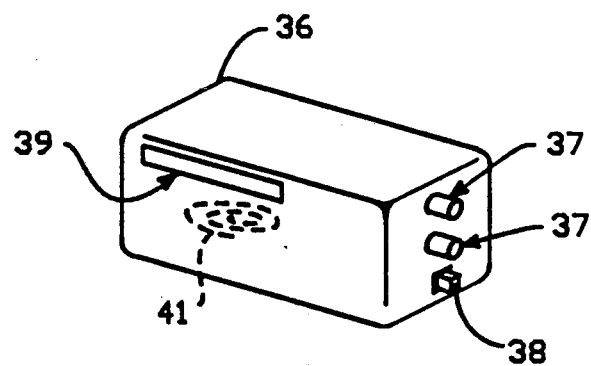
FIG. 6 is a perspective view of an electrical connector for FIG. 5.

Radio frequency power or signals may be delivered to or received from the coil via direct connection or a matching network as suggested by the above '372 patent. However, FIG. 4 illustrates an alternative embodiment where an inductive coupling indicated by the coil pattern 33 at the ends 16 and 17 may be utilized. Referring now to both FIGS. 5 and 6, a secondary coil 33 is illustrated with its insertion direction 34 as it would be placed in the primary coil receptacle box 36 which includes adjustment of knobs 37 and a standard RF connector 38 similar to that shown in the '372 patent. However, there is a slot 39 into which the connector 33 may be inserted to inductively couple to the primary coil 41 which is inside the box 36. The other end 17 may be conductively connected to ground or itself have a secondary coil.

Figure 7:
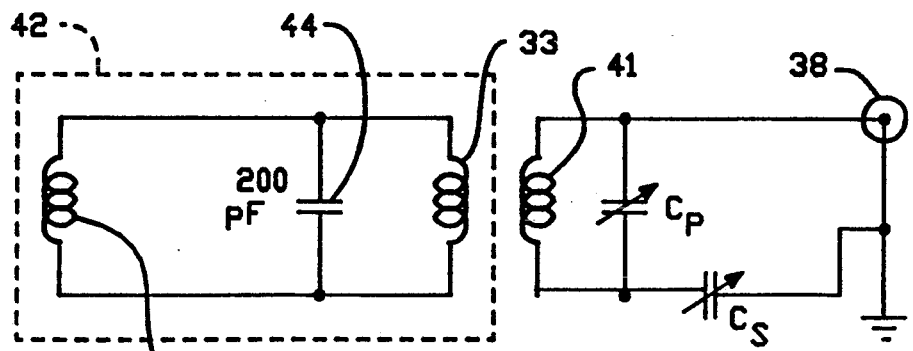
FIG. 7 is a circuit diagram showing the connection of FIG. 5 to FIG. 6.

FIG. 7 shows the circuit within a dashed box 42 as being the full coil assembly which is the inductance 43 of the copper band itself, a capacitor 44 which is mainly the capacitance of the secured ends of the band and then the secondary coil band 33. This couples to the primary coil 41 which is coupled to the adjustable parallel and series capacitors $C_p$ and $C_s$ which then go to the RF line 38. The adjustable capacitors provide for matching the impedance of the coil 10 represented in the block 42 to that of the transmitting/receiving RF cable 38.

Thus an improved shoulder coil has been provided for use in MRI.

What is claimed is:

1. A shoulder coil assembly having a predetermined magnetic axis for transmitting and/or receiving signals from a human shoulder produced in a magnetic resonance imaging apparatus comprising:

inductive pickup coil means for substantially surrounding said human shoulder including a thin flexible, unitary, continuous band of conductive material substantially entirely covered with a flexible protective material, the central portion of said band being shaped to conform to the side of the human thorax and pass around the base of the arm, including when the band is laid out flat in substantially a single plane, a substantially 180 degree turn in said central portion around an axis perpendicular to said plane, the ends of the band terminating in connectors for connection to a radio frequency cable for injection and/or extraction of the signals, said protective cover having facing interiors provided with mutually adhering surfaces which, when fastened together provide a conforming fit of the band to the top of the shoulder being imaged.

2. An assembly as in claim 1 including sufficient padding integral to the protective cover to place the conducting band a distance from the shoulder appropriate for good RF magnetic field uniformity.

3. An assembly as in claim 2 where said protective material is cloth, and said padding material is flexible foam.

4. An assembly as in claim 1 where said connectors include secondary coil means through which said signals may locally be injected or extracted.

5. An assembly as in claim 4 including means for adjusting the mutual inductance between a primary coil and the secondary coil means for matching the impedance of said band to that of the transmitting/receiving RF cable.

6. An assembly as in claim 1 where the ends of said band are joined by a clip means for locally assuring adherence of said band near said ends.

* * * * *